(12) United States Patent
Li et al.

(10) Patent No.: US 6,451,296 B1
(45) Date of Patent: Sep. 17, 2002

(54) ENHANCED EFFICACY ALUMINUM-ZIRCONIUM ANTIPERSPIRANTS AND METHODS FOR MAKING

(76) Inventors: Zijun Li, 313 Hazel Ave., Westfield, NJ (US) 07090; Jawahar Chunilal Parekh, 62 Hillside Ave., Livingston, NJ (US) 07039

( * ) Notice: Subject to any disclaimer, the term of this patent is extended or adjusted under 35 U.S.C. 154(b) by 0 days.

(21) Appl. No.: 09/496,168

(22) Filed: Feb. 1, 2000

(51) Int. Cl.[7] .............................. A61K 7/34; A61K 7/38; C07F 19/00
(52) U.S. Cl. ..................... 424/66; 424/68; 424/401; 556/27
(58) Field of Search ..................... 424/66, 68, 401; 556/27

(56) References Cited

U.S. PATENT DOCUMENTS

| | | | |
|---|---|---|---|
| 3,507,896 A | 4/1970 | Jones et al. ................ 260/448 |
| 3,981,986 A | 9/1976 | Rubino ........................ 424/47 |
| 4,359,456 A | 11/1982 | Gosling et al. ............... 424/68 |
| 4,871,525 A | * 10/1989 | Giovanniello et al. ...... 423/463 |
| 5,179,220 A | 1/1993 | Katsoulis et al. ............. 556/27 |
| 5,330,751 A | * 7/1994 | Curtin et al. ................. 424/66 |
| 5,356,609 A | 10/1994 | Giovanniello ............... 423/462 |
| 5,626,827 A | 5/1997 | Barr et al. ................... 423/412 |
| 5,939,057 A | * 8/1999 | Provancal et al. ............ 424/66 |
| 6,126,928 A | * 10/2000 | Swaile ........................ 424/65 |
| 6,149,897 A | * 11/2000 | Swaile ........................ 424/65 |

FOREIGN PATENT DOCUMENTS

| EP | 789554 | 8/1997 |
|---|---|---|
| WO | WO 98/58626 | 12/1998 |

\* cited by examiner

Primary Examiner—Porfirio Nazario-Gonzalez
(74) Attorney, Agent, or Firm—Arthur J. Plantamura

(57) ABSTRACT

Stable aluminum-zirconium antiperspirant compositions in polyhydric alcohol solution with enhanced efficacy were made by direct reaction in aqueous solution of a soluble aluminum salt, a zirconium compound, a polyhydric alcohol, aluminum metal and optionally an amino acid buffer, and maintaining the solution at 100–140° C. to form a 20–45% by weight concentration of aluminum-zirconium complexes on an anhydrous basis. A solid product can be obtained by spray drying the product solution.

26 Claims, 1 Drawing Sheet

ENHANCED EFFICACY ALUMINUM-ZIRCONIUM ANTIPERSPIRANTS AND METHODS FOR MAKING

This invention relates to a method of making aluminum-zirconium antiperspirants of enhanced efficacy in polyhydric alcohols and to the products obtained.

BACKGROUND OF THE INVENTION

Aluminum halide antiperspirant compounds are well known. The addition of zirconium compounds to aluminum complexes generally enhances the efficacy of the antiperspirants because of the depolymerization of aluminum species in the presence of zirconium. As the concentration of zirconium increases, more monomeric and polymeric aluminum cations are formed, and a change in the structure of the polymers is also observed. This accounts for improvements in aluminum-zirconium antiperspirants over the use of aluminum antiperspirants alone.

Alcohol-soluble aluminum complexes are disclosed in U.S. Pat. No. 3,507,896 to Jones et al, and can be made by reacting aluminum metal with aluminum chloride or hydrochloric acid at 75–110° C. in the presence of a polyhydric alcohol and water. There are no restrictions on the amount of water that can be used.

Current processes for making aluminum-zirconium (hereinafter Al and Zr) antiperspirants involves making Al and Zr salts in aqueous solutions separately, combining the solutions, adding polyhydric alcohols either before or after combining the solutions and evaporating excess water. Such methods require the evaporation of large amounts of water from the dilute solutions and thus is not economical. In order to make activated Al—Zr antiperspirants, the combined solution is held at elevated temperatures for lengthy periods. Such heating in aqueous solution forms high molecular weight polymers of Zr species. The presence of such polymers reduces the effectiveness of antiperspirant compositions.

The Al species in aluminum or aluminum-zirconium antiperspirants are generally of three types; a) fast reacting $Al^{3+}$ ion which consists of monomers, designated as $Al^a$; b) slower reacting polyhydrolysis species, designated as $Al^b$; and c) very slow reacting high molecular weight polymers and amorphous solids, designated as $Al^c$.

$AlCl_3.6H_2O$ consists of 96% monomeric $Al^a$ species, whereas 50% by weight aluminum chlorhydroxy solutions contain over 95% of high molecular weight $Al^c$ polymeric species.

The prior art teaches several methods of determining the degree of polymerization of Al complexes.

One of these is known as high performance liquid chromatography (HPLC). The highest molecular weight Al species are eluted first, known as Band I. Bands II and III designate intermediate molecular weight Al complexes. Band IV designates the lowest molecular weight Al complexes, including monomers and probably dimers. Band V designates small molecules that do not include Al. The relative area of one or more peaks is determined in order to characterize the distribution of polymeric species in the Al complexes formed.

The relative peak areas or peak regions, as a percentage of total peak area, is obtained by dividing the integral curve area of a particular peak or region by the sum of the integral curve areas of all of the resonance peaks. Desirable Al—Zr antiperspirant compositions exhibit more than 60% of aluminum species of Bands III and IV, and 0% to 5% of Band I.

Another method of determining the degree of aluminum complex polymerization includes Ferron Analysis, which reacts the Al complexes with a ferron reagent, and characterizes the complexes on the basis of three species types; as low molecular weight $Al^{3+}$ monomers, hereinafter $Al^a$; as intermediate molecular weight complexes from the dimer up to about $Al_{13}$, hereinafter $Al^b$, and as high molecular weight aluminum hydroxide complexes, hereinafter $Al^c$, which takes the longest time to react with the ferron reagent. It is an objective of the present invention to provide an aluminum-zirconium antiperspirant of enhanced efficacy with an increased amount of depolymerized aluminum species, i.e., wherein at least 25%, and preferably more than 40%, of the aluminum species are monomeric.

Still another method used is $^{27}Al$ nuclear magnetic resonance (NMR) to determine the structure of aluminum in the Al—Zr antiperspirant. For the present application, data were collected from about +160 to −160 ppm.

Most of the known methods of preparing antiperspirants of enhanced efficacy involve heating diluted basic aluminum chlorhydroxide solutions. The HPLC chromatogram of the salt has a peak area ratio of Band III to Band II of at least 0.5. However, the solution is unstable, and over time the Band III to Band II area is lowered to 0.3 or less. However, Band IV, which includes $Al^{3+}$ monomers, is not mentioned in the prior art. A higher Band IV will increase the effectiveness of the antiperspirant.

A method of producing the present Al—Zr complexes from an aluminum halide and zirconium oxyhalide, together with a polyhydric alcohol, that has a Band III plus Band IV of at least 60%, and preferably of about 80 to 90%, would increase efficacy as an antiperspirant and thus would be highly desirable. It is also desirable to obtain a stable solution of an Al—Zr composition in a concentration of 20–45% by weight.

SUMMARY OF THE INVENTION

The present method comprises forming a reaction mixture of an aqueous solution of a soluble aluminum salt, a zirconium compound, an amino acid buffer, a polyhydric alcohol having at least two carbon atoms to which at least two hydroxyl groups are attached and mixtures thereof, and aluminum metal, maintaining the reaction mixture at a temperature of about 100–140° C. to provide an Al—Zr complex in the polyhydric alcohol at a concentration of about 20–45% by weight on an anhydrous solid basis. The product obtained is characterized by a high Band III and Band IV content, having a HPLC relative area of at least 60%, and 0% to 5% of the total chromatogram peak area eluting at the shorter retention times of Band I. This composition contains monomeric $Al^a$ species of at least 25%, and preferably of above 40%, and is stable in solution at concentrations of at least 20%, and preferably 30–35% by weight.

BRIEF DESCRIPTION OF THE DRAWING

The FIGURE is a graph of $^{27}Al$ nuclear magnetic resonance of a product of the invention.

DETAILED DESCRIPTION OF THE INVENTION

Figure 1:
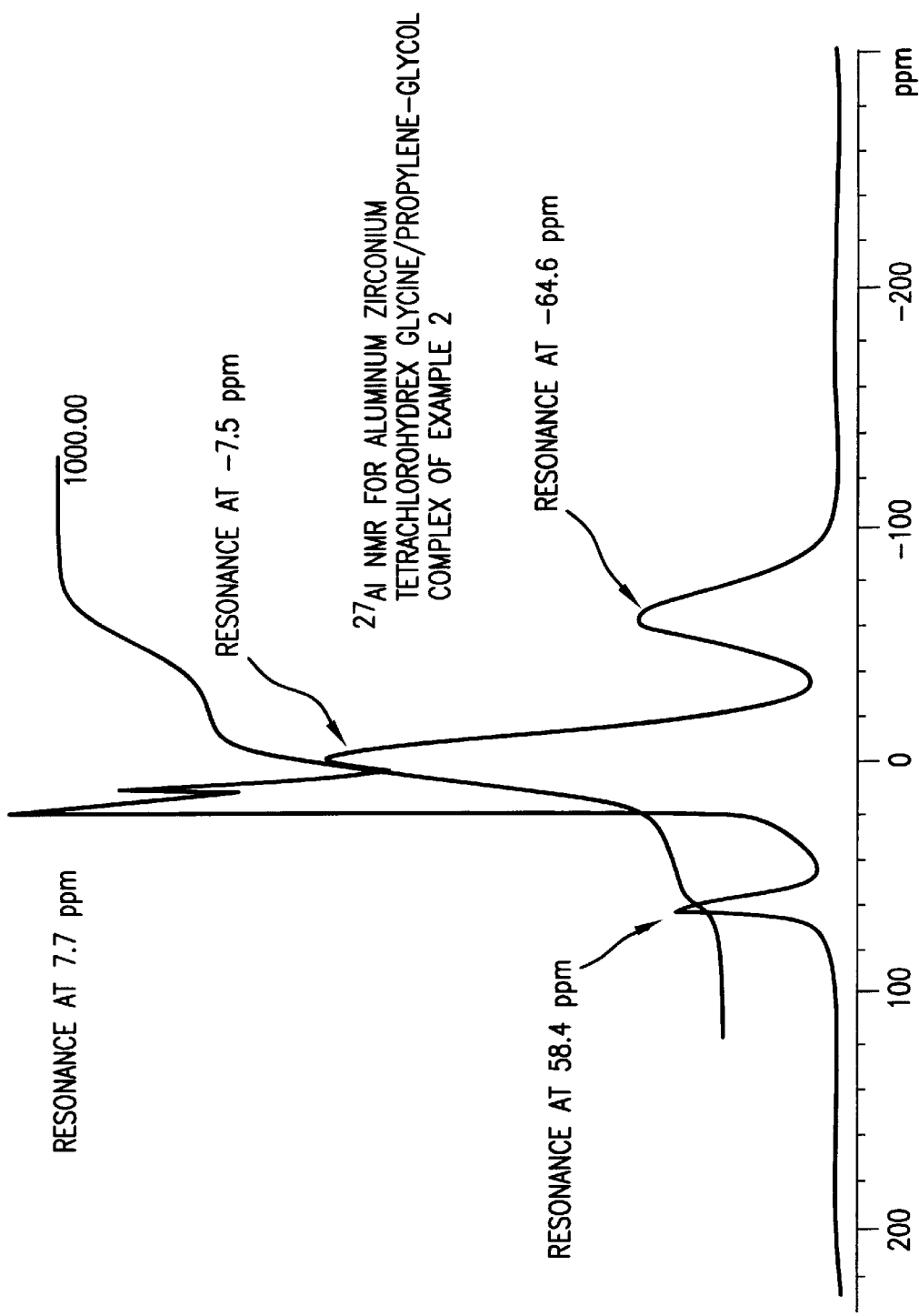

The present invention provides a direct method for making polyhydric alcohol antiperspirant solutions of Al and Zr directly from soluble aluminum salts and zirconium compounds in the presence of particular polyhydric alcohols, metallic aluminum and a minimum amount of water. An amino acid buffer can also be added. When the amount of water used is minimal, the Al and Zr species present are much less polymerized than when large amounts of water are used. Heating in particular polyhydric alcohols is believed to stabilize the Zr polymers from further polymerization, as observed in aqueous solution. The present process further eliminates the need for evaporating large amounts of water from two dilute solutions.

The soluble aluminum salts herein can be formed directly from an aluminum salt, or can be formed in situ from powdered aluminum and an appropriate acid. Suitably such acids have the formula $H_yX$, wherein X is a member of the group consisting of halide, nitrate, sulfate, carbonate and perchlorate, and y has the valence of X.

Suitable zirconium compounds have the formula $ZrO(OH)_{2-ab}(X)_b$, wherein b may vary from 0.5 to 2; a is the valence of X; (2–ab) is greater than or equal to zero; and X is as defined above.

Suitable polyhydric alcohols have at least two carbon atoms, preferably from 2 to 12 carbon atoms, to which at least two hydroxy groups are attached, and mixtures thereof. Liquid polyaliphatic or polyhydroxy compounds are also suitable. Suitable examples include propylene glycol, butylene glycol, diethylene glycol, dipropylene glycol, glycerin, sorbitol and the like. The amount of polyhydric alcohol employed is 20 to 70% by weight of the final antiperspirant solution. A concentration of 35–60% by weight is preferred. They should be liquid at room temperature.

Amino acids are optionally used as a buffer to maintain a suitable pH in the product solution. Suitably the amino acids useful herein have a number of amino groups that equals the number of carboxyl groups in the molecule, such as glycine. Other suitable amino acid compounds include alkaline, alkaline earth or metal glycinates, aluminum and magnesium hydroxyglycinate and the like. DL-valine, alaine arginine, L-proline and mixtures thereof can also be used. The buffer should provide a solution pH of at least 2.5.

The invention further prepares Al—Zr complexes having a minimum of high molecular weight polymers of Al, thus providing the enhanced efficacy Al—Zr antiperspirant compositions.

The aluminum-zirconium active formed is monitored by high performance liquid chromatography (HPLC) which separates the polymeric aluminum species by size. Thus larger, higher molecular weight molecules elute in Band I, and Bands II to IV have progressively smaller species. Desirably, 0% to 5% of the product elutes at the shorter retention times of Band I. At least 60% of the aluminum species corresponds to Bands III and IV. It is preferred that at least 25% of the aluminum species in the product is $Al^a$ species, and preferably this percentage is up to 30–45%. Such solutions are much more effective than when higher molecular weight Al polymeric species are present.

A Phenominex column is used to obtain the HPLC chromatograph. A sample of a 2% by weight solution of Al is filtered through a 45 micron filter and chromatographed within 5 minutes using a 0.01N nitric acid solution as the mobile phase.

The antiperspirant composition of the invention contains more than 60%, preferably 70–85% and up to 90% of Al species corresponding to Bands III and IV, and 0% to 5% corresponding to Band I.

Another method of measuring the distribution of polymeric Al species is by conventional ferron analysis.

An NMR technique is also used for the characterization of aluminum species and interactions between metals and polyhydric alcohol molecules.

A reaction mixture was made of Al powder, aluminum halide solution or aluminum nitrate solution, zirconium oxychloride, an amino acid and a polyhydric alcohol. Standard aluminum halide solutions are available at a concentration of about 28%, but other concentrations may be used.

The reaction is continued at a temperature of about 100–140° C. until an Al:Zr ratio of 2–10, and a solution solids concentration of about 20–45% by weight is obtained, not including the glycine and polyhydric alcohol. The preferred Al:Zr ratio is 3.3–3.6, with a preferred solids concentration of 30–35% by weight. The desired product has an HPLC chromatography peak area corresponding to Bands III and IV of over 60%, and the peak area corresponding to Band I of from 0% to 5%.

The product solution can be spray dried if desired to form a dry product.

The invention will be further described in the following examples, but the invention is not meant to be limited to the details described therein. In the examples, all parts and percentages are by weight. Aluminum chloride was used as a 28% by weight solution, at 32°Be. Zirconium oxychloride was used as a solid, which is commercially available. The aluminum powder was 99% min. purity and 75% of the aluminum particles passed through a 325 mesh screen. However, other forms of aluminum, including pellets, wire and the like can be used. The use of aluminum in forms other than a powder will extend the reaction time.

EXAMPLE 1

In this example, the atomic ratio of Al:Zr is 3.4.

125 Parts of aluminum chloride, 230 parts of zirconium oxychloride and 78 parts of glycine were dissolved in 400 parts of propylene glycol (PG). The solution was placed in a conical flask with a reflux condenser, and the reaction mixture was heated to 115° C. 58 Parts of aluminum powder was added over a period of about one hour. After 4 hours, the reaction mixture was filtered and the clear solution collected.

Chemical analysis of this solution was: % Al, 6.11; % Zr, 6.25; % glycine, 7.06; % Cl, 7.85%; % PG, 39.14. The ratio of Al:Zr was 3.4. The ratio of glycine:Zr was 1.4.

Ferron analysis: 34.6% $Al^a$; 8.5% $Al^b$ and 56.9% $Al^c$.

HPLC results: 2.6% Band I; 4.8% Band II; 44.1% Band III and 48.5% Band IV.

EXAMPLE 2

In this example, the amount of PG and the ratio of glycine to zirconium were kept similar to that of Example 1, but the Al:Zr atomic ratio was 5.3, higher than that of Example 1.

200 Parts of aluminum chloride, 170 parts of zirconium oxychloride and 45 parts of glycine were dissolved in 400 parts of PG. The solution was heated at 115° C. when 62 parts of aluminum powder was added over a period of 1.25 hours. The reaction was complete in 75 minutes. The solution was filtered.

Chemical analysis was as follows: % Al, 7.38; % Zr, 4.77; % glycine, 4.50; % Cl, 8.56; % PG, 37.34; Al:Zr 5.3 and ratio Glycine:Zr, 1.2.

Ferron analysis: 27.4% $Al^a$, 8.8% $Al^b$ and 63.7% $Al^c$.

HPLC, 0.8% Band I; 24.6% Band II; 34.0% Band III and 40.6% Band IV.

$^{27}Al$ NMR spectra of the solution was collected using a Tecmag Libra System SDS 360-1. Data from −160 to +160 ppm was collected. The results are shown in the FIGURE.

A comparison with the results of Example 1 shows a higher amount of Zr produced lower molecular weight Al complexes.

EXAMPLE 3

252 Parts of aluminum chloride and 104 parts of zirconium oxychloride were mixed with 460 parts of PG. 63 Parts of Al powder was added to the clear solution at about 115° C. over a period of 50 minutes. The reaction was complete in 70 minutes. The solution was filtered.

Chemical analysis: % Al, 7.40; % Zr, 2.70; % Cl, 7.70; % PG, 45.00; and ratio Al:Zr 9.4.

Ferron analysis: 32.9% $Al^a$; 5.2% $Al^b$ and 61.9% $Al^c$.

HPLC: 0.7% Band I; 31.4% Band II; 43.5% Band III and 24.4% Band IV.

EXAMPLE 4

270 Parts of aluminum chloride, 110 parts of zirconium oxychloride and 25 parts of glycine were mixed with 440 parts of PG. The mixture was heated to 115° C. when 68 parts of aluminum powder were added over about 45 minutes. A clear solution was formed in three hours at 117° C.

Chemical analysis was as follows: % Al, 8.2; % Zr, 3.01; % Cl, 8.7; % glycine, 2.52; % PG, 40.85; Al:Zr, 9.4 and Glycine:Zr, 1.0.

Ferron analysis: 37.9% $Al^a$; 7.3% $Al^b$; and 54.8% $Al^c$.

HPLC results: 0% Band I, 39.2% Band II, 29.0% Band III and 31.8% Band IV.

A comparison with the results of Example 3 show that the presence of glycine produced lower molecular weight Al species.

EXAMPLE 5

50 Parts of aluminum chloride, 333 parts of zirconium oxychloride and 109 parts of glycine were dissolved in 400 parts of PG. 49 Parts of aluminum powder was added to the solution at 115° C. The reaction mixture was filtered and the clear solution spray dried to give a white powder.

The chemical analysis was as follows: % Al, 7.90; % Zr, 15.59; % Cl, 13.87; % glycine, 23.80; % PG, 17.00; Al:Zr 1.7 and Glycine:Zr, 1.4.

Ferron analysis was 47.7% $Al^a$; 13.4% $Al^b$; and 38.9% $Al^c$.

HPLC results: 0.8% Band I; 5.4% Band II; 39.3% Band III; and 54.5% Band IV.

EXAMPLE 6

125 Parts of aluminum chloride, 230 parts of zirconium oxychloride and 78 parts of glycine were mixed with 600 parts of PG. The reaction mixture was heated to 118° C. and 58 parts of aluminum powder was added over 5 minutes. The reaction was complete in 7 hours at about 125° C. The reaction mixture was filtered.

Chemical analysis: % Al, 3.72; % Zr, 5.91; % Cl, 7.59; % glycine, 6.64; % PG, 55.36; ratio Al:Zr 2.2 and ratio glycine:Zr, 1.4.

Ferron analysis: 48.5% $Al^a$; 18.5% $Al^b$; and 33.0% $Al^c$.

HPLC results: 0% Band I; 3.2% Band II; 27.1% Band III; and 69.7% Band IV.

Comparing the above results and those of Example 5 to those of other examples, at a lower Al:Zr atomic ratio, more depolymerized Al species are produced.

EXAMPLE 7

125 Parts of aluminum chloride solution, 230 parts of zirconium oxychloride and 55 parts of glycine were mixed with 600 parts of PG. 58 parts of aluminum powder was added to the solution at 115° C. over 10 minutes. The reaction was stopped after four hours. The reaction mixture was filtered and analyzed.

Chemical analysis: % Al, 5.74; % Zr, 5.71; % Cl, 7.49; % glycine 5.31; % PG 52.10, Al:Zr ratio 3.5 and Glycine:Zr ratio 1.1.

Ferron analysis: 30.7% $Al^a$; 9.8% $Al^b$ and 59.5% $Al^c$.

HPLC results: 0.3% Band 1; 4.9% Band II; 54.3% Band III and 40.5% Band IV.

EXAMPLE 8

125 Parts of aluminum chloride, 230 parts of zirconium oxychloride and 78 parts of glycine were mixed with 600 parts of PG. The reaction mixture was heated to about 117° C. when 58 parts of aluminum powder was added within 2 minutes. The reaction was continued for 6.5 hours at about 118° C. and then filtered.

Chemical analysis: % Al, 4.90; % Zr, 4.94; % Cl, 6.45; % glycine, 6.17; % PG, 52.48, Al:Zr ratio was 3.4 and glycine:Zr ratio was 1.5.

Ferron analysis: 37.6% $Al^a$; 8.5% $Al^b$; and 53.9% $Al^c$.

HPLC results: 0% Band I; 2.2% Band II; 53.0% Band III and 44.9% Band IV.

Comparing the above results to those of Example 1, higher amounts of PG produced higher amounts of low molecular weight Al species.

Further, comparing the above results to those of Example 7, wherein the Al:Zr atomic ratio was the same and the amount of PG was the same, and the amount of glycine was varied, higher amounts of glycine produced more low molecular weight Al species.

EXAMPLE 9

125 Parts of aluminum chloride, 230 parts of zirconium oxychloride, and 78 parts of glycine were mixed with 400 parts of PG. The solution was heated at 115° C. when 58 parts of aluminum powder was added over 40 minutes. The reaction was continued for 4.5 hours when the reaction mixture was filtered. The solution was spray dried to a white powder, which was analyzed as follows:

% Al, 10.50; % Zr, 11.00; % C; 14.03; % glycine, 13.22; % PG, 32.60; ratio Al:Zr 3.3 and ratio glycine to Zr, 1.5.

Ferron analysis was 34.7% $Al^a$; 5.7% $Al^b$; and 59.6% $Al^c$.

HPLC results: 1.3% Band I; 9.2% Band II; 41.7% Band III and 47.8% Band IV.

EXAMPLE 10

96 Parts of hydrochloric acid (33% by weight of HCl), 230 parts of zirconium oxychloride and 38 parts of glycine were mixed with 400 parts of PG. The solution was heated to about 115° C. and 65 parts of aluminum powder was added over 35 minutes. The reaction was continued for 3.5 hours and the reaction mixture was filtered. A clear, light yellow solution was obtained. Analytical results were as follows:

Chemical analysis: % Al, 6.24; % Zr, 6.41; % Cl, 8.56; % glycine, 3.53; % PG, 41.02; Al:Zr ratio 3.4; and glycine:Zr ratio 0.7.

Ferron analysis: 36.4% $Al^a$; 11.9% $Al^b$; and 51.7% $Al^c$.

HPLC results: 1.4% Band I; 20.7% Band II; 43.3% Band III; and 34.6% Band IV.

Thus at low glycine concentration, the amount of low molecular weight aluminum species, as measured by HPLC, was reduced.

EXAMPLE 11

$^{27}$Al NMR spectra data of the solutions of some of the Examples were collected as in Example 2. The results are given in the Table below.

TABLE

| Sample | Resonance Line Area Of −10 to +10 ppm | Resonance Line Area Of 62.5 to 63.5 ppm |
|---|---|---|
| Example 1 | 43.4 | 0 |
| Example 2 | 39.5 | 0 |
| Example 4 | 36.4 | 0 |
| Example 6 | 43.9 | 0 |
| Example 7 | 32.7 | 0 |
| Example 8 | 43.3 | 0 |

Thus 30 to 50% of the total area under the spectrum +160 to −160 ppm is contained in a resonance line at −10 to +10 ppm, and essentially 0% of the total area is contained in the resonance line at 62.5 to 63.5 ppm.

The polyhydric alcohol solutions of aluminum-zirconium complexes made by the direct process are highly desirable for enhanced efficacy antiperspirants, and are suitable for making clear gel products.

Although the present invention has been described in terms of specific embodiments, the invention is not to be so limited. Various changes can be made to the compositions used while still obtaining the benefits of the invention. Thus the invention is only to be limited by the scope of the appended claims.

We claim:

1. A method of preparing a stable polyhydric alcohol solution of an aluminum-zirconium antiperspirant solution having enhanced efficacy by having a high proportion of lower molecular weight aluminum complex species comprising heating an aqueous solution of an aluminum salt with a zirconium compound having the formula $ZrO(OH)_{2-ab}(X)_b$ wherein b can vary from 0.5 to 2; a is the valence of X; (2−ab) is greater than or equal to zero; and X is a member selected from the group consisting of halide, nitrate, perchlorate, carbonate or sulfate ion in the presence of from 20 to 70 percent by weight of a polyhydroxy alcohol having at least two carbon atoms to which at least two hydroxy groups are attached, and mixtures thereof, and aluminum metal at a temperature of about 100–140° C. to obtain an aluminum-zirconium complex in the polyhydric alcohol to a concentration of about 20 to 45% by weight on an anhydrous basis.

2. A method according to claim 1 wherein the aluminum salt is a halide, nitrate, sulfate, carbonate or perchlorate of aluminum.

3. A method according to claim 2 wherein said aluminum salt is formed in situ from a corresponding inorganic acid.

4. A method according to claim 1 wherein the zirconium compound is zirconium oxychloride.

5. A method according to claim 1 wherein the aluminum-zirconium solution additionally includes an organic buffer selected from the group consisting of an amino acid having an equal number of amino and hydroxyl groups in the molecule or an alkaline or metal salt of said amino acid and mixtures thereof.

6. A method according to claim 5 wherein the pH of the solution is at least 2.5.

7. A method according to claim 2 wherein the aluminum salt is a halide or a nitrate.

8. A method according to claim 1 wherein the aluminum:zirconium atomic ratio is from 10:1 to 1:10.

9. A method according to claim 1 wherein the reaction is carried out so that the amino acid to zirconium molecular ratio is 0:1 to 2:1.

10. A method according to claim 9 wherein the amino acid is glycine.

11. A method according to claim 1 wherein the aluminum and zirconium to anion mol ratio is from 0.9 to 2.1

12. A method according to claim 1 wherein the monomeric aluminum species is from 25 to 55%, intermediate molecular weight aluminum species is from 0 to 20%; and high molecular weight aluminum species is from 30 to 75%.

13. A method according to claim 1 wherein the solution has a $^{27}$Al nuclear magnetic resonance spectrum wherein 30 to 50% of the total area under the spectrum +160 to −160 ppm is contained in a resonance line at −10 ppm to +10 ppm and in which the area of the resonance line at 62.5 to 63.5 ppm is from 0% to 5% of the total area.

14. A method according to claim 1 wherein the product solution is spray dried to form a solid product.

15. A method according to claim 1 wherein the reaction is carried out so that the molecular weight ratio of aluminum:zirconium is 3.4 to 3.6.

16. A method according to claim 10 wherein the reaction is carried out so that the molecular weight ratio of glycine:zirconium is 1.4 to 1.6.

17. A method according to claim 1 wherein the reaction is carried out so that the molecular weight ratio of polyhydric alcohol:aluminum is 2.0–2.5.

18. An aluminum-zirconium product having HPLC Band III and Band IV relative area values of at least 60 percent.

19. An aluminum-zirconium product according to claim 18 having a Band I relative area value of from 0% to 5 percent.

20. An aluminum-zirconium product according to claim 18 wherein the Band III and Band IV relative area values are at least 75 percent.

21. An aluminum-zirconium product according to claim 18 wherein the Band III and IV relative area values are at least 90 percent.

22. An aluminum-zirconium product according to claim 18 wherein the distribution of aluminum monomer ($Al^a$) is from 25 to 55 percent; the aluminum oligomer content ($Al^b$) is from 0 to 20 percent; and the aluminum polymer content ($Al^c$) is from 30 to 75 percent, and the sum of $Al^a$ and $Al^c$ species is at least 70 percent.

23. An aluminum-zirconium product according to claim 18 wherein the concentration in alcohol solution is from 20 to 45 percent by weight on an anhydrous basis.

24. An anhydrous aluminum-zirconium product according to claim 18.

25. A method of inhibiting perspiration comprising applying an aluminum zirconium product prepared according to claim 1 to the axilla.

26. An aluminum-zirconium product having HPLC Band III and Band IV relative area values of at least 60 percent and wherein the distribution of aluminum monomer ($Al^a$) if from 25 to 55 percent; the aluminum oligomer content ($Al^b$) is from 0 to 20 percent; and the aluminum polymer content ($Al^c$) is from 30 to 75 percent, and the sum of $Al^a$ and $Al^c$ is species is at least 70 percent.

* * * * *